United States Patent [19]

Marquis

[11] 4,064,170

[45] Dec. 20, 1977

[54] PREPARATION OF METHYLENE-BRIDGED POLYARYLPOLYAMINE MIXTURES

[75] Inventor: Edward T. Marquis, Austin, Tex.

[73] Assignee: Texaco Development Corporation, New York, N.Y.

[21] Appl. No.: 723,276

[22] Filed: Sept. 15, 1976

[51] Int. Cl.$^2$ ............................................. C07C 85/24
[52] U.S. Cl. ................................................. 260/570 D
[58] Field of Search ................................... 260/570 D

[56] References Cited

U.S. PATENT DOCUMENTS 3,996,283   12/1976   Knofel ................................. 260/570

FOREIGN PATENT DOCUMENTS 1,228,495   4/1971   United Kingdom ................. 260/570

Primary Examiner—Robert V. Hines
Attorney, Agent, or Firm—Carl G. Ries; Thomas H. Whaley; James L. Bailey

[57] ABSTRACT

An improved process for the preparation of methylene-bridged polyarylpolyamines by the acid catalyzed condensation reaction of an aromatic primary amine and formaldehyde is disclosed wherein nitrilotriacetic acid is employed as the catalyst system. An aromatic primary amine and formaldehyde are mixed and reacted at an elevated temperature in the presence of a catalytic amount of nitrilotriacetic acid which provides a resulting reaction product that does not have to be subjected to neutralization procedures or filtration for catalyst removal as heretofore required. The reaction product mixtures of methylene-bridged polyarylpolyamines has excellent color and can be employed without further treatment as epoxy curing agents, urethane cross linkers, as precursors for the preparation of corresponding methylene-bridged polyarylpolyisocyanates, and the like. The employment of nitrilotriacetic acid also leads to the completion of the condensation reaction in relatively short periods of time.

6 Claims, No Drawings

PREPARATION OF METHYLENE-BRIDGED POLYARYLPOLYAMINE MIXTURES

BACKGROUND OF THE INVENTION

1. Field of the Invention

This invention relates to the preparation of aromatic amines and more particularly pertains to an improved process for the preparation of polymethylene polyarylpolyamine mixtures by the acid catalyzed condensation reaction of an aromatic primary amine and formaldehyde.

2. Description of the Prior Art

The condensation reaction of aromatic primary amines, such as aniline, substituted anilines, etc., and formaldehyde carried out in the presence of an acid-containing material catalyst at elevated temperatures is well known and has been employed for many years in procedures for the preparation of methylene-bridged polyarylpolyamine mixtures useful as epoxy resin curing agents, urethane cross-linkers, precursors for corresponding polyisocyanates, and the like. These known processes are amply described in the literature and many patents, for example U.S. Pat. Nos. 2,683,730; 2,950,263; 3,012,008; 3,344,162; 3,362,979; 3,277,173; 3,496,229 and Belgian Patent 648,787, to name a few.

Generally speaking, procedures for preparing polymethylene polyarylpolyamine mixtures include mixing and reacting an excess of an aromatic primary amine, such as aniline, substituted anilines, and the like, with formaldehyde at an elevated temperature above about 105° C in the presence of a catalytic amount of a strong mineral acid, e.g., hydrochloric acid. The reaction is usually complete in about 4 to 5 hours and provides a resulting reaction product of polymethylene polyarylpolyamine containing a diamine portion in admixture with higher functionality higher molecular weight methylene-bridged polyarylpolyamines. The diamine portion of the reaction product mixture can be substantially controlled by varying several reaction conditions, such as the molar ratio of aromatic primary amine to formaldehyde. Moreover, as known, the positional isomer content of the diamine portion of the reaction product, namely the 2,2'-, 2,4'-, and 4,4'-, diamine isomers can be varied by varying reaction conditions and employing different types of acid-containing materials as the catalyst.

However, known procedures employing strong mineral acids as catalysts in such condensation reaction procedures not only suffer from the difficulty of requiring long reaction times but also require the employment of corrosive-resistant reaction and handling equipment, inasmuch as such acids are highly corrosive. Moreover, the employment of such mineral acids require neutralization of the crude condensation reaction product mixtures with a basic material such as caustic to produce the desired polymethylene polyarylpolyamine mixtures. Neutralization brings on the additional difficulties of by-product removal and disposal.

Several procedures are known in the art which do not suffer from the aforementioned disadvantages. For example, U.S. Pat. No. 3,362,979 to Bentley describes a procedure for the preparation of methylene-bridged polyphenylpolyamine mixtures by carrying out the condensation reaction of aniline and formaldehyde in the presence of solid acid-siliceous catalysts such as silica-alumina cracking catalysts. As disclosed, the employment of solid acid-siliceous catalysts such as silica-alumina eliminates the necessity of employing corrosive-resistant processing apparatus and the necessity of neutralizing the reaction product mixture to provide the desired methylene-bridged polyphenylpolyamine product mixtures. The patent further teaches that the employment of such solid catalysts results in the production of polyphenylpolyamine mixtures having diamine portions that contain greater amounts of the 2,4'- isomer than obtained by conventional strong mineral acid catalyzed condensation reaction procedures. Yet such solid acid siliceous catalyst procedures suffer from other disadvantages such as slow condensation reaction rates and difficulty in separating the solid catalyst materials from the resulting reaction product mixtures. These solid catalysts are employed in finely powdered form and separating them from the crude condensation reaction product mixtures, such as by filtration, has been found to be difficult.

U.S. Pat. No. 3,496,229 to Powers et al. also teaches a process for preparing polymethylene polyarylpolyamine mixtures that does not suffer from the aforementioned disadvantages of requiring the use of corrosive-resistant processing apparatus and the neutralization of the resulting reaction product. Patentees teach a process for the aforementioned condensation reaction of an aromatic primary amine and formaldehyde which is carried out in the presence of a low-level synergistic catalyst system which is comprised of a mixture of an acid which has a pKa value (measured at 25° C in water) of 1.5 to 5 and a catalytic amount of neutral salt of a metal and a nonmetal. More particularly, the acid is employed in an amount sufficient to provide a molar ratio of the aromatic amine reactant to the acid of about 100 to 1 to about 200,000 to 1 and the neutral salt is present in an amount in the range of 0.01 to 10%. However, the procedure suffers from the same disadvantage as the aforementioned procedure employing solid acid-siliceous catalysts in that the neutral salts of the catalyst system must be removed from the resulting reaction product mixture, such as by filtration. The required employment of the neutral salt in the co-catalyst system and subsequent necessity of removal from the reaction product are added expense and time consuming requirements of such procedures.

I have now discovered a process for the preparation of methylene-bridged polyarylpolyamine mixtures by the catalyzed condensation reaction of an aromatic primary amine and formaldehyde which does not suffer from any of the aforementioned disadvantages associated with the aforementioned procedures. The process of the present invention can be carried out in less expensive reaction and handling apparatus and does not require neutralization of the reaction product or filtration of any catalyst material, particularly when low concentrations of catalyst are used. The inventive process may be conducted at relatively high temperatures for relatively short periods of time which greatly improves the economics for preparing polymethylene polyarylpolyamine mixtures.

SUMMARY OF THE INVENTION

In accordance with the present invention, methylene-bridged polyarylpolyamine mixtures are prepared by mixing and reacting an aromatic primary amine of the formula

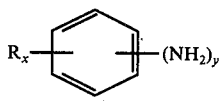

where x is 0 to 3, y is 1 to 2 and R is selected from a group consisting of alkyl having from 1 to 10 carbon atoms, lower alkoxy having 1 to 10 carbon atoms, chlorine, bromine or nitro; and formaldehyde at a temperature within the range of from about 100° C to about 350° C under a pressure of from atmospheric to about 300 psig for a time period of about 10 minutes to about 4 hours in the presence of a catalytic amount of nitrilotriacetic acid. Most unexpectedly, the use of nitrilotriacetic acid as a catalyst material for the condensation reaction leads to very fast reaction rates which provides a resulting methylene-bridged polyarylpolyamine product mixture of excellent viscosity, diamine isomer distribution, functionality and color. Since in many cases only low amounts of catalyst need be used, there is no necessity to separate any excess catalyst remaining, if any be present. The resulting reaction product can be readily purified by known techniques, such as by simple flash distillation, to remove excess unreacted aromatic primary amine and water of reaction, and used directly as a precursor in conventional phosgenation reactions for the preparation of corresponding methylene-bridged polyarylpolyisocyanate mixtures, or as epoxy curing agents, urethane cross-linkers, and the like. The product polyamine dissolves readily and completely in solvents such as chlorobenzene in the concentration ranges which are generally employed for commercial phosgenation processes.

This invention is not aware of any prior art specifically disclosing the utilization of nitrioltriacetic acid alone as a catalyst for the condensation reaction of an aromatic primary amine with formaldehyde in the preparation of aromatic polyamines. As noted hereinbefore, U.S. Pat. No. 3,496,229 teaches employment of a low level synergistic catalyst system in such condensation reactions which consists of an acid and at least 0.01 weight percent of a neutral salt. The process of this invention does not require the employment of nitrioltriacetic acid with any other catalytic material such as the neutral salts described in U.S. Pat. No. 3,496,229. Also, surprisingly, there is no necessity to neutralize the crude condensation reaction product mixture of the present invention to obtain the desired polymethylene polyarylpolyamine product mixture and the unneutralized polyamine mixture is readily and completely soluble in a solvent such as chlorobenzene at the concentrations used in commercial phosgenation procedures (6–10 weight percent amine in chlorobenzene). Such results were most unexpected in view of known prior art procedures employing acids in catalyst systems.

DETAILED DESCRIPTION OF THE INVENTION

Any aromatic primary amine having the formula set forth hereinabove may be used in accordance with the present invention. Suitable aromatic primary amines include for example, aniline, orthotoluidine, meta-toluidine, para-toluidine, ortho-ethyl aniline, meta-ethyl aniline, para-ethyl aniline, ortho-propyl aniline, meta-propyl aniline, para-propyl aniline, ortho-butyl aniline, meta-butyl aniline, para-butyl aniline, ortho-tertiary butyl aniline, meta-tertiary butyl aniline, para-tertiary butyl aniline, ortho-decyl aniline, meta-decyl aniline, para-decyl aniline, 2,6-xylidene aniline, 2,4-xylidene diamine, 2,6-diethyl aniline, 2,4-diethyl aniline, 2-methyl-6-ethyl aniline, ortho-anisidine, meta-anisidine, para-anisidine, ortho-phenetidine, meta-phenetidine, para-phenetidine, 2,3,5-trimethyl aniline, 2-methyl-3-ethyl-6-octyl aniline, 2-methyl-4-phenyl-6-ethyl aniline, meta-benzyl aniline, para-benzyl aniline, para-phenoxy aniline, ortho-chloro aniline, meta-chloro aniline, para-chloro aniline, ortho-bromo aniline, meta-bromo aniline, para-bromo aniline, ortho-nitro aniline, meta-nitro aniline, para-nitro aniline, 2,4-toluylene diamine, 2,6-toluylene diamine, meta-phenylene diamine and the like.

Especially preferred are aniline and substituted anilines of the formula:

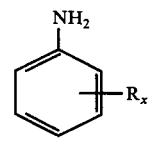

wherein x is 0 or 1 and R is lower alkyl having from 1 to 10 carbon atoms, chlorine, bromine or lower alkoxy having from 1 to 10 carbons.

For the purposes of brevity only, the aromatic primary amines contemplated for use in the present invention and described hereinabove will be referred to as "aromatic amines".

The process of the invention is preferably carried out by mixing and reacting an excess amount of aromatic amine and formaldehyde in the presence of a catalytic amount of nitrilotriacetic acid which is preferably used in an amount of within the range of about 0.1 to about 3.5 weight percent, based upon the weight of aromatic amine charged. Experiments have shown that the employment of less than about 0.1 weight percent is ineffective while the employment of more than about 3.5 weight percent results in reaction products with lowered amine content. It can be readily understood that optimal amounts for a given reaction are dependent upon many processing variables controlled as desired, e.g., the molar ratio of formaldehyde to aromatic amine, specific temperatures and pressures, desired reaction times, the type of formaldehyde, and the like. Optimum amounts of nitrilotriacetic acid employed for a given reaction can be readily determined by one having ordinary skill in the art without undue experimentation.

The molar ratio of aromatic amine to formaldehyde employed may be varied within comparatively wide limits. Preferably, about 1 to 10 moles of aromatic amine are employed per mole of formaldehyde employed. This is particularly preferred where aniline is used in the condensation reaction of the invention. As known, in employing the lower aniline:formaldehyde molar ratios, such as ratios of from about 1:1 to about 2:1, the higher functionality, higher molecular weight polymethylene polyphenylpolyamines (triamines, tetramines, etc.) will be formed preferentially, and the yield of higher polymers is approximately equal to or in excess of the yield of the diamine portion, methylene diphenylamine. However, as progressively larger amounts of aniline are used, the yield of the diamine portion is progressively increased at the expense of higher polymer yield. Thus, with aniline to formaldehyde molar ratios of from about 2:1 to about 10:1, the reaction product will be composed in the majority of the diamine. The same is true for other aromatic amines noted hereinabove.

In carrying out the process of the invention, formaldehyde may be employed in any of its commercially available forms. Thus, formalin, paraformaldehyde, "stabilized" methanol solutions of formaldehyde, etc. may be employed interchangeably without adversely affecting the process. Moreover, the inventive process can be carried out in accordance with any technique known in the art so as to provide an intimate admixture of the aromatic amine, formaldehyde and nitrilotriacetic acid catalyst at elevated temperatures in liquid phase. For example, the nitrilotriacetic acid can be initially mixed with the formaldehyde, preferably employed in its commerically available "stabilized" methanol solution form, and admixed with the aromatic amine in conventional batch or continuous reactor systems whereby the admixture is exposed to the reaction conditions described more particularly hereafter.

The reaction may also be conducted in the presence or the absence of a solvent. When a solvent is employed, it may be any of the conventionally known hydrocarbon solvents or chlorinated hydrocarbons, such as aromatic or aliphatic solvents boiling within the range of from about 100° to about 350° C. The solvents should be employed in an amount sufficient to provide a single phase solution of the amine reaction product. However, inasmuch as the process of the invention is carried out in the presence of an excess amount of aromatic amine and the condensation reaction produces water, the employment of other solvents is not preferred.

As mentioned hereinbefore, reaction conditions for the inventive process include a temperature within the range of from about 100° C to about 350° C under a pressure sufficient to maintain the reaction in liquid phase, e.g. usually within the range of from atmospheric to about 300 psig for a time period of from about 10 minutes to about 4 hours. An unexpected advantage of the inventive process is that higher temperatures can be employed resulting in polymethylene polyarylpolyamine mixtures of excellent color without adversely lowering the 4,4'-isomer content in the diamine portion. Preferably, temperatures within the range of from about 100° to about 250° C are employed. It is also preferred to carry out the reaction under autogenous pressure, such as by carrying out the reaction in a sealed environment. Inasmuch as the formaldehydearomatic amine condensation reaction is exothermic, it is preferred to add the formaldehyde at a rate such that the temperature of the reaction can be maintained.

Another unexpected advantage of the process of the invention is the fact that the reaction rate is greatly increased. Under the aforementioned reaction conditions the reaction is usually complete in about 10 minutes to about one-half hour utilizing conventional equipment. Yet if desirable, reaction times of up to four hours can be employed without adverse affects being observed.

Although, as mentioned hereinbefore, nitrilotriacetic acid can be employed as the catalyst in the process of the invention in an amount of up to about 3.5 weight percent, basis weight of aromatic polyamine present, equal effectiveness of the catalyst is surprisingly present when lower amounts are used. In addition, an added benefit results when say 0.1–1.0 weight percent of catalyst is used. In such case one need not then filter off the catalyst and the polyamine may be used as such. Doing away with the added step of filtration is an obvious process advantage.

The reaction product mixture of methylene-bridged polyarylpolyamines prepared in accordance with the above-described condensation reaction can be recovered from the resulting crude condensation reaction mixtures very easily by the employment of simple conventional techniques such as flash distillation to strip off water of reaction, impurities such as methanol (if present) and excess unreacted aromatic amine. These techniques are well known to those skilled in the art and will not be described herein in detail. As noted above, one of the primary advantages of the present invention is that the reaction product mixture of methylene-bridged polyarylpolyamines does not have to be filtered or further treated to remove catalyst employed in the condensation reaction when low catalyst concentrations are employed. The reaction product mixture has an excellent color, and, if desired, can be readily employed as a precursor for the preparation of corresponding methylene-bridged polyarylpolyisocyanate mixtures employing conventional phosgenation techniques. In this regard, another advantage of the present invention is the fact that the reaction product mixture is more readily soluble in solvents conventionally employed in such phosgenation techniques, such as monochlorobenzene. The phosgenation techniques referred to are well known in the art and amply described in the literature. Therefore a detailed discussion of such techniques will not be set forth herein.

The invention will be further illustrated by the following specific examples which are given by way of illustration and not as limitations.

EXAMPLE I

To a 1-l., stirred, stainless steel clave was added 372 g. aniline (4.0 moles) and 12.0 g nitrilotriacetic acid (NTA) 3.2% basis aniline) and 60 g of formaldehyde (as 37% formalin, 2.0 moles). The clave was flushed with nitrogen and heated to 140° C and held there with stirring for 4 hours. The product was stripped of water on a rotary evaporator using aspirator vacuum and a boiling water bath for the rotating flask. The mixture was filtered hot to remove traces of solids and the aniline stripped under high vacuum. The product amine consisted of an aromatic amine mixture with the isomer distribution in the diaminodiphenylmethane portion being 81.2% 4,4'-diaminodiphenylmethane (DADPM), 17.7% 2,4'-DADPM, 0.9% 2,2'-DADPM and 0.2% unknown.

EXAMPLE II

Using the apparatus, procedure and quantities of reagents as described above in Example I except that only 3.7 g NTA catalyst was used and the reaction temperature was 180° C, in the dimer portion of the polyamine was found 74.2% 4,4'-DADPM, 23.0% 2,4'-DADPM, and 2.8% 2,2-DADPM.

EXAMPLE III

Using the apparatus and procedure described in Example 1 except that only 1.9 g NTA catalyst (0.5% basis aniline charged) was used and the reaction mixture was heated to 180° C for 4 hours, the amine product weighed 324 grams and there were no solids to filter during this workup. The isomer distribution in the dimer portion of the product was 71.9% 4,4'-DADPM, 25.6% 2,4'-DADPM, and 2.5% 2,2'-DADPM.

EXAMPLE IV

The method of Example 1 was followed with the exceptions that 11.2 g NTA was used as catalyst (3.0% basis aniline) and the reaction was heated to 140° C for 4 hours. This afforded an aromatic amine product with 3.6% 2° amine, 3.6% N-methyl aniline type by-product and 92.8% diaminodiphenylmethane isomers and higher polyamines. Filtration during work up afforded about 22 g of solids that the IR spectrum indicated were an NTA amine salt. The isomer distribution in the dimer portion of the aromatic amine product was 80.2% 4,4'-DADPM, 18.5% 2,4'-DADPM and 1.2% 2,2'-DADPM and 0.1% unknown. Total amine analysis gave 9.65 meq/g. and Kjeldahl nitrogen analysis gave 13.6% nitrogen.

I claim:

1. In the process for the preparation of methylene-bridged polyarylpolyamine mixtures by the condensation reaction of an aromatic primary amine having the formula:

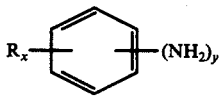

wherein $x$ is 0 to 3, $y$ is 1 to 2 and R is selected from the group consisting of alkyl having from 1 to 10 carbon atoms, lower alkoxy having 1 to 10 carbon atoms, chlorine, bromine or nitro, and formaldehyde carried out in the presence of an acid-containing material catalyst at elevated temperatures the improvement comprising:

employing nitrilotriacetic acid as said acid-containing material catalyst, wherein said aromatic primary amine having said formula and formaldehyde are mixed with a catalytic amount of said nitrilotriacetic acid and heated to a temperature of about 100° C to about 350° C under a pressure within the range of from atmospheric to about 300 psig for a time period of from about 10 minutes to about 4 hours; and recovering the methylene-bridged polyarylpolyamine mixture from the resulting reaction product.

2. The process of claim 1 wherein nitrilotriacetic acid is employed as said catalyst in an amount of up to about 3.5 weight percent, based upon the weight of said aromatic primary amine present.

3. The process in accordance with claim 1 wherein said mixture is heated at a temperature of from 100° C to about 250° C.

4. The process in accordance with claim 1 wherein said nitrilotriacetic acid is present in an amount of from about 0.1 to about 1.0 weight percent, based upon the weight of said aromatic primary amine present.

5. The process in accordance with claim 1 wherein said aromatic primary amine is selected from the group consisting of aniline and substituted anilines, each having the formula:

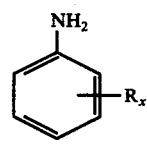

wherein $x$ is 0 or 1 and R is lower alkyl having from 1 to 10 carbon atoms, chlorine, bromine or lower alkoxy having from 1 to 10 carbon atoms.

6. The process of claim 5 wherein said aromatic primary amine is aniline.

* * * * *